United States Patent [19]

Newkirk et al.

[11] Patent Number: 5,109,710
[45] Date of Patent: May 5, 1992

[54] DIRECT FILTER INJECTION SYSTEM FOR GAS CHROMATOGRAPHS

[75] Inventors: Matthew S. Newkirk; David M. Human, both of San Antonio, Tex.

[73] Assignee: Southwest Research Institute, San Antonio, Tex.

[21] Appl. No.: 541,816

[22] Filed: Jun. 21, 1990

[51] Int. Cl.⁵ .......................................... G01N 30/20
[52] U.S. Cl. ................................. 73/863.11; 73/23.41
[58] Field of Search ............... 73/863.11, 23.25, 23.41, 73/31.07

[56] References Cited

U.S. PATENT DOCUMENTS

| | | | |
|---|---|---|---|
| 3,327,520 | 6/1967 | Stapp, Jr. | 73/23.25 X |
| 3,401,552 | 9/1968 | Ruchelman | 73/23.41 |
| 3,463,012 | 8/1969 | McKinney et al. | 73/864.81 X |
| 4,293,316 | 10/1981 | Block | 73/31.07 X |
| 4,344,917 | 8/1982 | Schorno | 73/23.25 X |
| 4,357,836 | 11/1982 | Kokesh | 73/863.11 |
| 4,710,354 | 12/1987 | Behar et al. | 422/78 X |
| 4,759,210 | 7/1988 | Wohltjen | 73/31.07 |
| 4,919,893 | 4/1990 | Bandurski et al. | 422/78 |

FOREIGN PATENT DOCUMENTS

| | | | |
|---|---|---|---|
| 721751 | 3/1980 | U.S.S.R. | 73/23.41 |
| 1418607 | 8/1988 | U.S.S.R. | 73/863.11 |

Primary Examiner—Hezron E. Williams
Assistant Examiner—Joseph W. Roskos

[57] ABSTRACT

An injector port assembly for direct injection of a solid filter test sample for gas chromatography analysis comprising and elongated thermally conductive injector tube having a perforated sample holding portion, and an injection port having a sealable entry opening into which the elongated injector tube is moveably inserted, a hot zone, a cool zone thermally insulated from the hot zone, a purge valve and a conduit for connecting said injection port in fluid communication with a gas chromatography column.

2 Claims, 2 Drawing Sheets

DIRECT FILTER INJECTION SYSTEM FOR GAS CHROMATOGRAPHS

BACKGROUND OF THE INVENTION

This invention relates to an apparatus and a method for direct chromatographic analysis of filter trapped analytes. Particularly the invention relates to an apparatus and method for receiving and injecting trapped volatiles directly from a solid filter medium into a gas chromatograph for analysis.

The field of chromatographic analysis has been generally limited to gaseous or liquid samples. It has been discovered that there is a need for a system which will allow chromatographic analysis of filters which have trapped solids or other materials such as volatiles thereon. There is a need in the area of environmental protection testing of exhaust gases such as with combustion engine emission testing. Specifically tests which use particulate filters to collect carbon soot, lubrication oil volatiles, fuel volatiles, and other components of the exhaust gases. Previous methods for exhaust emissions testing, such as indirect testing of collected exhaust constituents, have been complicated, expensive and time consuming. Prior to the present invention, chromatography devices were not well suited for direct analysis of filter collected particulate matter and volatiles.

In other fields there have been injection systems and methods for thermal analysis of geological samples to obtain information useful in petroleum exploration. One example is disclosed in U.S. Pat. No. 4,357,836 issued to Kokesh Nov. 9, 1982. In this method a solid sample such as small granules or powdered of geological specimens are placed in a quartz tube the ends of which are enclosed by gas permeable quartz felt. The quartz tube is wrapped with a wire heater coil which holds the quartz tube in which the sample is contained. The heating coils and sample are inserted into an injection port a portion of which is cooled with a complex fluid circulation system. Fluid such as air is cooled and then blown through baffles arranged in an annular space surrounding the port. A carrier gas is introduced into the port through a gas inlet while the sample is in the cooled zone. Gas blows through the port and exists through the gas chromatograph column for about 1 to 2 minutes until stabilization is reached. Subsequently, the heater coil probe holding the glass or quart tube with the sample therein is moved to a portion of the port for heating. The temperature of the geological sample material is then raised either to accomplish thermal extraction in the range 100° C. to about 400° C., to accomplish pyrolysis at temperatures of about 350° to about 1000° C. The gaseous materials generated from the sample mix with the carrier gas and flow into the gas chromatography column. This apparatus and method is not well suited for direct filter analysis and is complex and cumbersome. It would require placement of the solid matter in granule form into a gas permeable quartz tube. The quartz tube must be carefully placed for holding in a heating coil probe. The system requires the use of special cooling circulation and apparatuses associate with that system. Moreover, there is a substantial waste of energy as the entire port is constructed of heat conductive material so that the cool zone and hot zone constantly work against each other. The cooling circulation system expends energy to remove the same heat energy which is expended in the hot zone for thermal extraction or pyrolysis.

Other complex probe sampling apparatuses and sample inlet instruments have also been previously disclosed. For example, U.S. Pat. No. 3,463,012 issued to McKinney, et al Aug. 26, 1969 and also U.S. Pat. No. 4,344,917 issued to Schorno Aug. 17, 1982 disclose devices which have many of the same drawbacks as discussed above. Both of those devices are constructed with a hot zone and a cool zone which are interconnected with thermally conductive material. The heat generated in the hot zone for thermal extraction must be either continuously or periodically removed using a cooling fluid circulation system. Solid samples are placed in quartz tubes having gas permeable quartz wool ends. The McKinney disclosure relies upon the escape of carrier gas through the inlet opening for stabilizing the system and Schorno relies upon the escape of carrier gas through the gas chromatograph column itself. None of these systems, methods or apparatuses is well suited for direct filter analysis.

Traditional methods of simulated distillation analysis to determine the components in the exhaust use a single time or temperature on the response cure to estimate the boiling point of the fuel (typically 369°). Any constituants shown in the gas chromatograph response below this temperature are considered to be unburned fuel and any constituants above are considered to be the lubricating oil. This can result in an inaccurate reading as some fuel components evaporate at higher temperatures and some oil constituents evaporate at lower temperatures.

SUMMARY OF THE INVENTION

Applicant's invention overcomes many of the deficiencies and inadequacies of prior injector instruments and systems by providing a direct filter injections port assembly having a cool zone which is thermally insulated from the hot zone. The hot zone is maintained at the desired elevated temperature using a heater block so that the sample can be heated quickly. A cold purge conduit and a purge valve are uniquely provided so that the port can be purged of oxygen and contaminants while the sample is in the cold zone. In other systems oxygen, air or other fluids may interfere with analysis and passing such materials directly into the lab or through the chromatography column can have detrimental consequences. A test filter can be directly placed into a perforated heat conductive holding tube without the need for the complexity of the quartz sample tubes. During operation the test filter material having trapped particulate matter and/or volatiles therein is inserted into a perforated end of the injector. The injector is inserted through a sealing septum so that the perforated end and the specimen filter are within the cool zone. The cool zone is uniquely and efficiently created without complex cooling systems by thermally insulating it from the hot zone. Inert carrier gas is injected through the injector, over the specimen filter and out through the perforations into the cool zone. The purge valve is opened to allow oxygen, air, water and other impurities to be quickly evacuated from the injection port. The purge valve is then closed and the injector is slipped through the sealing septum so that the perforated end containing the specimen filter is placed in the hot zone which is maintained at the desired elevated temperature. The filter specimen is inside a thermally conductive perforated holder to facilitate heat transfer by conduction as well as by radiation and convection. This quickly raises the temperature of the specimen filter for thermal extraction by converting the volatiles to be tested into gaseous materials which are carried via the carrier gas through a conduit into the chromatographic column.

Thus, the complex cooling system of prior devices is not required, the use of special quartz sample tubes is not required, the purging is accomplished quickly without passing potentially deteriorating agents through the chromatographic column and without releasing the purged gas directly into the laboratory atmosphere. The sample is raised to extraction temperature quickly because it is contained within a heat conductive injector tube and does not rely entirely on convection or radiation for heat transfer. The additional benefit of conductive heat transfer is achieved and there is no need for wrapping the sample carrier with heat generating coils.

The invention also relates to an improved device and method for determining the components in the sample by comparing the response of the sample to actual responses of the fuel and of the lubricating oil used in the engine from which the test sample was obtained.

BRIEF DESCRIPTION OF THE DRAWINGS

The above described objects and advantages as well as other objects and advantages of Applicant's invention will become apparent with reference to the following drawings and detailed description of the invention in which like numerals represent like elements and in which.

DETAILED DESCRIPTION OF THE INVENTION

Figure 1:
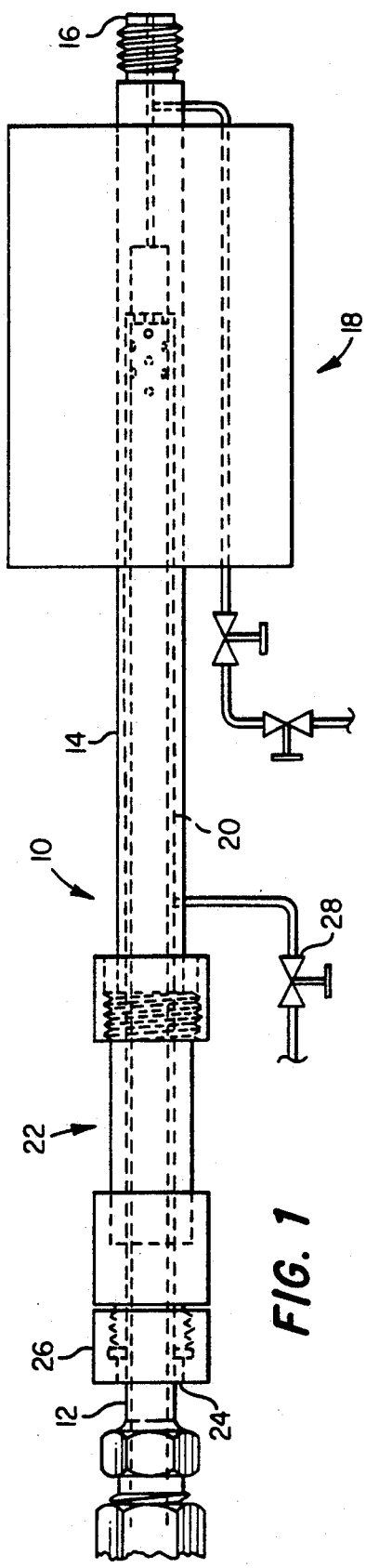
FIG. 1 is a side plan view of the injection port and injector tube assembly of the present invention.

The inventive injection system is composed of two major components which can be observed with reference to FIG. 1 which is a side plan view of injection port assembly 10 having injector 12, shown partially with hidden lines, inserted into the injection port 14. The injection port 14 consists of a connector 16 which is adapted for air tight connection to a gas chromatography column (not shown). Adjacent the chromatograph connector 16 is a hot zone 18. There is an open passage 20 (shown with hidden lines) interconnecting the hot zone 18 with a cool zone 22. Preferably the open passage 20 is substantially continuous through the cool zone 22 and at least partially into the hot zone 18. Injection port 14 has an injector entry opening 24 adjacent the cool zone 22. The entry opening 24 is fitted with an entry seal means 26. Preferably between the cool zone 22 and the hot zone 18 there is a cold purge valve means 28 which is in fluid communication with the interior passage 20 of port 14.

Figure 2:
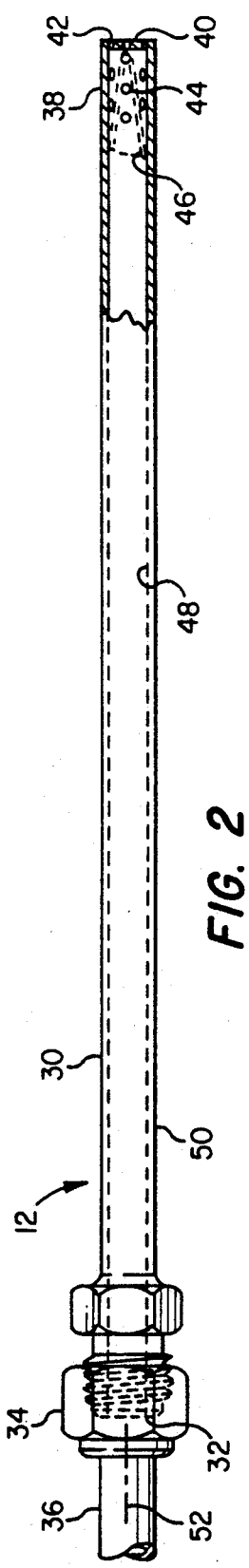
FIG. 2 is a side plan view with a partial section of the injector tube with the sample specimen filter depicted with phantom lines.

With reference to FIG. 2 the details of injector 12 can be better understood. Injector 12 comprises an elongated tubing 30 which is constructed of a substantially non-reactive material and advantageously having good thermal conductivity characteristics. In the preferred embodiment elongated tube 30 is constructed of stainless steel which will not adversely produce oxides which could interfere with the chromatography analysis. The stainless steel construction advantageously resist deterioration and has a high thermal conductivity in the temperature ranges of about 0° C. to 450° C. which has been found to be the useful range for direct filter injection according to the present invention.

Injector 12 is constructed with a receiving orifice 32 which is made with a easily removable "air tight" fitting 34 for rapid connection and removal of a inert carrier gas supply line 36. While fitting 34 is shown in the preferred embodiment of FIG. 2 as a threaded fitting, it may be another suitable construction such as a slip fitting nozzle which is sized and adapted for receiving a flexible inert gas supply tubing 36 in an "air tight" manner. At the opposite end of the elongated tubing 30, a sample filter holding chamber 38 is constructed according to the present invention with an end cap 40 which partially obstructs the flow of carrier gas through tubing 30 of injector 12. End cap 40 is formed with perforations 42 to allow carrier gas to exit tubing 30 in the proximity of holding chamber 38. This obstruction to the flow insures that the carrier gas adequately mixes with any gas from a sample filter 46 hold in chamber 38. Preferably sample holding chamber 38 is further provided radially perforations 44 or a series of drilled holes 44 spaced apart and extending back from the distal end cap 40 a short distance. Preferably the injection tube is about 6.5 inches (16.5 cm) long with an outside diameter of about 0.25 inches (0.6 cm). The perforations 42 and 44 are about 0.03 inches (0.08 cm) in diameter and extend back from end cap 40 about 0.38 inches (0.95 cm).

In operation a specimen filter 46 shown in FIG. 2 with phantom lines, would be inserted through orifice 32 when fitting 34 and inert gas tubing 36 is removed. The specimen filter 46 is moved through the interior of elongated tube 30 and positioned within sample holding chamber 38 adjacent end cap 40 and perforations 42 and 44. In operation the injector 12 and port 14 of assembly 10 will be horizontally oriented such that no special construction is required to maintain sample filter 46 within holding chamber 38. However, it has been found according to present inventive method for direct filter injection, that filter specimen 46 can be beneficially sized and formed, as by bending or folding so that a small amount of holding friction results between sample specimen 46 and the hollow interior 48 of elongated tubing 30.

Elongated tubing 30 is provided with a substantially smooth exterior surface 50 which has substantially consistent dimensions along the entire length of elongated tubing 30 so that sliding sealing engagement can be maintained between injector 12 and entry seal means 26 of port 14 when the injector 12 is inserted therein. After the filter specimen 46 is placed within chamber 38 inert gas supply line 36 can be quickly and sealingly reattached.

It should be noted that the construction of injector 12 is preferably symmetrical about an axis 52 such that sealed sliding engagement along smooth surface 50 can be most easily achieved. Preferably tube 30 is a cylindrical tube so that radial orientation of tube 30 within sealing means 26 does not result in problems with sealing or other alignment difficulties.

Figure 3:
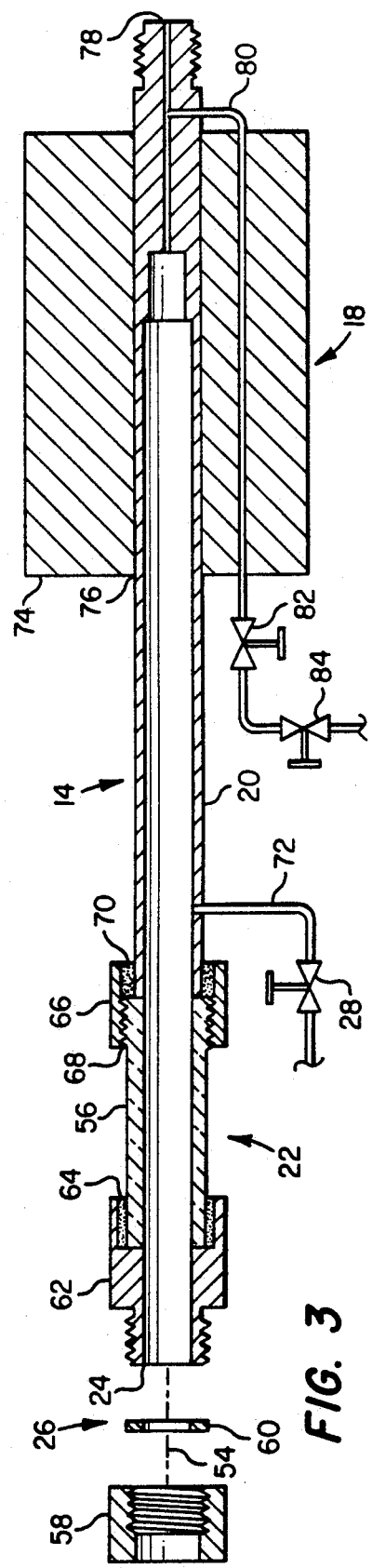
FIG. 3 is a side section view taken along the center line of the injector port showing the details of construction and materials of the injection port.

With reference to FIG. 3, which is a cross sectional view of port 14 along vertically through axis 54 thereof, the details of construction of port 14 can be better understood. The cool zone 22 is advantageously thermally insulated from the other parts of the port 14. Preferably the cool zone is constructed of heat insulative material along its entire length. In the preferred embodiment shown in FIG. 3 cool zone 22 is constructed of a ceramic tube 56. About 1½ inches (3.8 cm) long. While the shape of port of 14 can be any symmetrical shape it is preferably cylindrically shaped having a minimum interior dimension in passage 20 which is greater than the exterior dimension of injector 12. It is also preferred that the interior passage 20 be shaped the same as injector tube 30 (i.e. generally cylindrical) and sized for easy slip fit even with substantial variations of differential temperatures, between the component parts; yet, allowing mechanical support along passage 20 without undue stress on sealing means 26. Thus, cool zone 22 and in particular ceramic tube 56 also preferably has an interior diameter substantially equal to or slightly less than that of passage 20 and is arranged in axial alignment along axis 54. Thus, for an injector tube with an O.D. of about ¼ inch a ceramic tube 56 will have an I.D. of about 5/16 inches (0.79 cm) and passage 20 will have an I.D. of about 0.3 inches (0.76 cm).

At one end of ceramic tube 56 is entry seal means 26 which is composed of entry seal collet 58, sealing septum 60, and entry coupling 62. Entry coupling 62 is affixed to ceramic tubing 56 at junction 64. Preferably a ceramic-to-metal epoxy can be used to rigidly and permanently hold entry coupling 62 together and in axial alignment with ceramic tube 56. The other end of ceramic tube 56 is attached to passage 20 with passage coupler 66 so that there is a ceramic to metal rigid fastening at junction 68, such fastening may be accomplished for example, with sealed threads 68 or with epoxy. Passage coupler 66 is fastened to passage 20 as by weld 70. It is important to reduce the impurities of the port to a minimum and for that reason either stainless steel welding or silver soldering is preferred for weld 70.

In the preferred embodiment purge valve 28 is interconnected with passage 20 using conduit 72. The position of the entry of conduit 72 is preferably between the cool zone 22 and the hot zone 18. As will be explained more fully below with respect to the operation of the port and injector assembly 10 this position allows for advantageous purging of oxygen, air, water vapor or other elements which may interfere with the chromatographic analysis.

Referring to the hot zone 18 of FIG. 3, it will be seen that in the embodiment shown the hot zone 18 is maintainable at an elevated temperature using a hot block which acts as a thermal heat reservoir and which is in thermal conductive contact at 76 with the exterior of passage 20 of port 14. Preferably passage 20 of port 14 is constructed of stainless steel which has good heat conduction properties and also is chemically non-reactive within the temperature range needed for thermal extraction of volatile solids from the filter. It has been found that previous apparatus using a coil heating source such as electrical resistant wire wrapped directly around the sample holder are more complex and subject to a greater likelihood of failure than Applicant's heat block 74. Applicant advantageously avoids such complexity and accomplishes rapid heat transfer due to its unique thermally conductive and perforated structure for sample chamber 38. Heat block 74 also has advantages of maintaining a substantially constant temperature over a period of time and has sufficient heating capability so that during operation the temperature in the hot zone 18 is maintained relatively constant even though the the sample and the sample holding chamber 38 are rapidly raised to the same temperature as the heat block. The volatiles in the sample filter are quickly gasified and are mixed with the inert carrier gas for direct injection into the gas chromatography column for analysis.

Leading from the end of passage 20 is a conduit 78 which is generally smaller in diameter than passage 20 and which extends from the passage 20 through connector 16 for fluid or gas tight interconnection with the inlet to the gas chromatograph. Conduit 78 is also maintained at the elevated hot zone temperature along a portion of its length so that the possibility of subsequent condensation of volatiles is reduced. Further in the preferred embodiment a splitter conduit 80 and splitter valves 82 and 84 are provided to remove any excess quantities of the mixture of carrier gas and extracted volatiles. The excess quantities can be directed for safe venting or for other purposes such as for doing additional tests of the gaseous components generated by the port assembly, or for adjusting the quantity of flow to the gas chromatographic column. Splitter valves 82 and 84 can also provide additional purge relief before the sample specimen is moved into the hot zone 18.

These and other advantages and constructions of the present invention will be more fully understood with reference to the drawings and with the following explanation of the gas port assembly the injection port assembly 10 of FIG. 1 set forth below. The invention is particularly useful in connection with direct injection of particulate laden filters such as those used in EPA exhaust emission testing. Typically such sample filters collect oxidized hydrocarbon materials typically referred to as soot as well as volitale solids from unburned fuel and lubricating oil. Such a particulate laden filter is obtained from the environmental testing. A portion of the test filter is folded and inserted into injector 12 through receiving orifice 32. The folded sample is pushed into the sample holding chamber 38 adjacent capped end 40.

Next the inert carrier gas supply line 36 is attached to the injector 12 via coupling 34 which as indicated previously is a threaded male and female fitting arrangement which can be tightened to insure sealing engagement. The carrier gas is flowed through the injector and across the sample and out through the perforated chamber 38. This allows the injector 12 to be purged of all oxygen or other gaseous contaminants. Next the purge valve 28 which is preferably a needle valve 28 is opened completely. The injector is inserted so that a sample containing chamber 38 resides within cool zone 22. Of course, the injector 12 is inserted through collet 58, septum 60, and injector entry opening 24. The collet 58 is tightened on septum 60 so that it is squeezed against the exterior surface 50 of injector 12 to form an air tight slideable connection. With perforated sample injector 12 is inserted approximately 1 inch into port 14 so that chamber 38 is in the cool zone while the carrier gas is flowing and while needle valve 28 is opened. Within a few seconds, the entire port 14 is purged of any oxygen, air or contaminants such as water vapor which may have entered the port 14 before injector 12 was inserted. During purging, the carrier gas flows into the port at room temperature so that no thermal extraction takes place. The purge gas which is a mixture of carrier gas and any oxygen or contaminants will not flow through the chromatography column because the column has significantly higher back pressure than the freely opened purge line 72. This avoids deterioration of the column and reduces the time required for stabilization. The purge gas flowing through purge line 72 and valve 28 can be collected or vented in an environmentally safe and acceptable manner without directly entering into the laboratory or test environment.

When all the oxygen has been eliminated from the system the purge valve 28 is closed and the injector 12 is pushed through the sliding seal septum 60 and into the hot zone 18. The sample is then rapidly heated through conduction between the heating block 74 and the stainless steel sample carrier 38. Heat is also transferred to a lesser degree through radiation and convection through the perforated end 38 including both the drilled holes 44 and the perforations 42. The temperature of the heat block 74 is preferably approximately 350° C. to cause the types of solid trapped volatiles found in EPA testing including both fuels and lubricating oils to become gasified. The gaseous sample and carrier gas mixture thus flows directly from the filter through conduit 78 and into the gas chromatography column for analysis. As noted earlier if the sample quantities are too great the splitter line 80 may be opened to allow a portion of the sample to splitter line 80 and valves 84 and 82 may be opened to allow a portion of the sample gaseous material to be directed elsewhere. Splitter line 80 is also heated by heat block 74 to reduce condensation problems.

It can be seen that the inventive direct filter injection system as disclosed allows direct analysis of the filtered particulate samples taken during EPA test cycles and the like. Prior devices for this purpose could not accomplish the accuracy of Applicant's device because of the failures due to inadequate purging of oxygen or other contaminants. Further, Applicant's device beneficially performs this analysis without a complicated cooling circulation system as has been done in other fields such as geological rocks testing for hydrocarbons discussed above. Many benefits are obtained from the use of a ceramic tube construction which uniquely and beneficially insulates the cool zone 22 from the heat produced in the hot zone 18. The ceramic material is an effective barrier to conductive heat transfer along metallic injection port 14. The ceramic material also insulates against convective heat transfer. The system uniquely uses purge valve 28 to avoid direct discharge of purged gas directly through the chromatographic column. This avoids premature deterioration and increases the accurate life span of the chromatographic column. The discharge of purge gases is safely controlled and does not depend upon discharge of purge gases back over the sealed entry, as with other previously described devices for other testing procedures. Thus Applicant's device avoids a "hit and miss" purging procedure and results in repeatable accurate testing.

Figure 4:
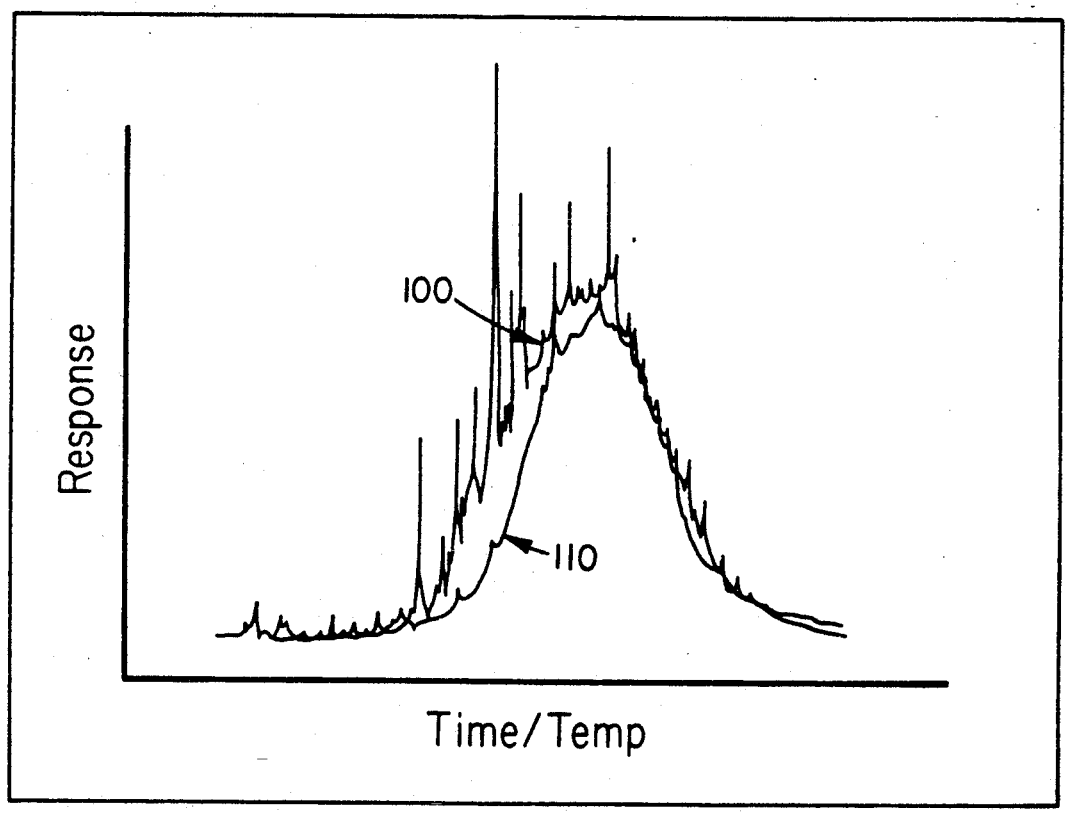
FIG. 4 is a graphical representation of the inventive method by which the actual contribution of oil sample to the response from the Direct Filter Injection Gas Chromatograph.

Referring now to FIG. 4, which is a graphical representation of a sample response from Direct Filter Injection Gas Chromatograph analysis according to the present invention, further advantages of the inventive device and method will be shown. A response curve 100 is obtained for a sample from the Direct Filter Injection Gas Chromatograph. A response curve 110 is obtained for an actual sample of the oil used, or of the identical type of oil used in the tested engine. The two curves 100 and 110 or the date establishing those curves is stored in a computer storage device. The curves or the date representing those curves is compared so that the actual contribution of the oil can be separated from the curve for the test sample at all temperatures during the response. The contribution from the fuel is then accurately determined without the use of a gross approximation for the temperature of evaporation. This comparison can be advantageously done mathmatically in a micro computer having memory means adequate for simultaneous recording of the date representing the two curves and having access means and comparison means for accessing the recorded curves and comparing them over the response range for determining the component provided by the fuel.

While the invention has been described in connection with a preferred embodiment, it is not intended to limit the scope of the invention to the particular form set forth, but, on the contrary, is intended to cover such alternatives, modifications, and equivalents as may be included within the spirit and scope of the invention as defined by the appended claims.

What is claimed is:

1. An injector port assembly for direct injection of a solid filter test sample for gas chromatography analysis comprising:
    a) an elongated thermally conductive injector tube having a perforated sample holding portion; and
    b) an injection port having a sealable entry opening into which said elongated injector tube is moveably inserted, comprising a hot zone, a cold zone removably attached to and thermally insulated from said hot zone, a purge valve means and means for connecting said injection port in fluid communication with a gas chromatography column.

2. An injection port comprising:
    a) a tubular structure defining a passage for accepting an injector tube having a sealable entry at one end of said defined passage;
    b) a ceramic tube adjacent to said sealable entry and in alignment with said defined passage and removably attached and thermally insulated from said sealable entry and a hot zone of said tubular structure;
    c) closeable vent means interconnected to said defined passage;
    d) a hot zone along said passage into which said injector tube may be slid for raising the temperature of said injector tube through conductive heat transfer; and
    e) conduit means in fluid communication with said hot zone of said defined passage for fluid communicative connection to a gas chromatography column.

* * * * *